Figure 1:
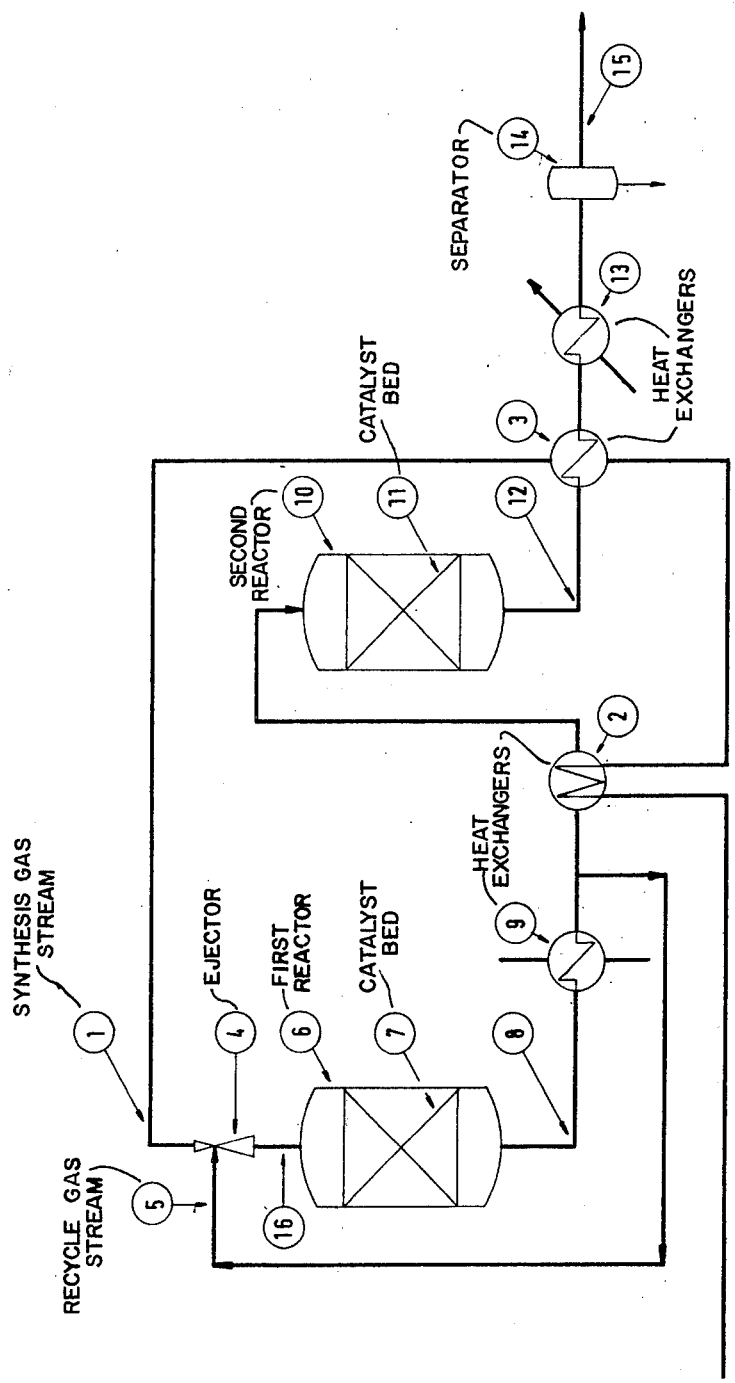

United States Patent [19]

Jørn

[11] 4,130,575

[45] Dec. 19, 1978

[54] PROCESS FOR PREPARING METHANE RICH GASES

[75] Inventor: Ernst Jørn, Lyngby, Denmark

[73] Assignee: Haldor Topsøe A/S, Søborg, Denmark

[21] Appl. No.: 624,818

[22] Filed: Oct. 22, 1975

[30] Foreign Application Priority Data

Nov. 6, 1974 [GB] United Kingdom ............... 47924/74
Apr. 22, 1975 [GB] United Kingdom ............... 16641/75

[51] Int. Cl.$^2$ .............................................. C07C 1/04
[52] U.S. Cl. .................... 260/449 M; 260/449.6 M; 48/187 R
[58] Field of Search .................... 260/449 M, 449.6 M

[56] References Cited

U.S. PATENT DOCUMENTS

| | | | |
|---|---|---|---|
| 2,345,957 | 4/1944 | Wirth et al. ........................ | 260/449.6 |
| 2,711,419 | 6/1955 | Melbourne et al. ......... | 260/449.6 M |
| 2,937,077 | 5/1960 | Faatz et al. ........................... | 423/654 |
| 3,854,895 | 12/1974 | Muller .................................... | 48/197 |
| 3,890,113 | 6/1975 | Child et al. ..................... | 260/449 M |
| 3,904,389 | 9/1975 | Banquy ............................ | 260/449 M |
| 3,922,148 | 11/1975 | Child ................................. | 260/449 M |
| 3,927,997 | 12/1975 | Child et al. ..................... | 260/440 M |
| 3,927,999 | 12/1975 | Child et al. ..................... | 260/449 M |
| 3,967,936 | 7/1976 | Tajbl et al. ..................... | 260/449 M |
| 4,005,996 | 2/1977 | Hausberger et al. .......... | 260/449 M |

OTHER PUBLICATIONS

Bienstock et al., Bureau of Mines, Report of Investigations 5841 (1961), p. 1-27.
Field et al., I & EC Product Research & Development vol. 3, No. 2 (1964) p. 150-153.

*Primary Examiner*—Howard T. Mars
*Attorney, Agent, or Firm*—Lawrence Rosen; E. Janet Berry

[57] ABSTRACT

Hydrogen and carbon oxides are reacted to form methane by passing an inlet stream of preheated methanation synthesis gas together with a recycle stream of product gas through a catalyst bed in an adiabatic methanation reactor. The inlet temperature is between 250° and 350° C, the outlet temperature between 500° and 700° C. The recycle stream is withdrawn from the outlet stream after the latter has been cooled to a temperature between 250° and 350° C and being, however, at least 50° C above the dew point. A preferred means for withdrawing the recycle stream is an ejector driven by the inlet stream or by added steam.

3 Claims, 2 Drawing Figures

PROCESS FOR PREPARING METHANE RICH GASES

This invention relates to a process for the production of a methane rich gas by methanation. In such a process carbon oxides and hydrogen are reacted to form methane in the presence of a catalyst. The invention relates particularly to a process for methanation of a gas having a high concentration of carbon oxides.

Methanation processes have been used for many years to remove traces of carbon oxides from ammonia synthesis gas. In recent years methanation processes have become of increasing importance for the production of methane rich gases suitable as substitutes for natural gas. In this way solid and liquid fossil fuels such as coal and fuel oils can be converted to substitute natural gas by a gasification process followed by methanation.

In such methanation processes the formation of methane from carbon oxides and hydrogen proceeds quickly to equilibrium in the presence of a catalyst and in accordance with either or both of the following reaction schemes:

(1) $CO + 3H_2 \rightarrow CH_4 + H_2O$ (2) $CO_2 + 4H_2 \rightarrow CH_4 + 2H_2O$ It is not very important to know which of above two reactions is the faster, since there will at the same time be an approach to equilibrium between carbon monoxide and carbon dioxide as follows:

(3) $CO + H_2O \rightleftarrows CO_2 + H_2$

The net reaction of methane formation whether by reaction (1) or (2) or both will be highly exothermic. Therefore, the temperature of the reactants and products will increase during the passage through a catalyst bed in an adiabatic reactor. On the other hand, such increasing temperature will tend to displace the equilibrium towards lower methane concentration. Consequently, complete or close to complete reaction will only be possible if the temperature increase is limited by cooling the reacting gas in one way or another, for instance by recycling of cooled product gas.

Recycling of cooled product gas for the purpose of reducing the temperature increase in an adiabatic methanation reactor has been used previously. For instance, the product gas has been cooled to a temperature of about 50° C. lower with subsequent removal of the steam condensate before recycling. Cooling to low temperatures is necessary since otherwise a conventional compressor could not be used for the recycling. However, such complete cooling of the product gas before recycling will result in a poor energy economy of the methanation process.

On the other hand, if the recycle gas is only moderately cooled, the recycle compressor should be designed so as to operate at high temperatures, for instance at 300° C. At such a temperature the energy economy would be good since steam condensation would not occur and the heat removed during the cooling could be efficiently utilized for high pressure steam production. However, a simple and yet safe compressor design for temperatures substantially above 150° C. is hardly known, and in any case would be complicated and expensive. Therefore, recycling of product gas at 300° C. would give compressor problems.

It is an object of the present invention to provide a methanation process in which the reactor is maintained cooler by recycling of cooled product gas without a preceding steam condensation and without the use of a compressor.

Accordingly, we provide a process for the production of a methane rich gas by adiabatically passing methane synthesis gas together with a stream of hot recycle product gas through at least one catalyst bed in which process the recycle gas stream is withdrawn from the product gas stream after having been cooled to a temperature above the condensation point of the product gas and in which process the recycle gas stream may be recycled by means of an ejector.

More specifically, we provide a process for the production of a methane rich gas in at least one adiabatically operated methanation reactor by combining an inlet stream of a preheated methane synthesis gas containing hydrogen and carbon oxides, especially carbon monoxide, and a recycle stream consisting of product gas from the methanation reactor, passing the combined streams through a bed of a methanation catalyst contained in the methanation reactor, and dividing the outlet stream into the recycle stream and a stream of product gas which may be passed on for further processing, or which may be collected and cooled for direct use, for instance as a substitute natural gas. The above objects of the invention are achieved if the methanation reactor is operated to provide the outlet stream at a temperature of between 500° C. and 700° C. after which the outlet stream is cooled to a temperature between 250° C. and 350° C. and being at the same time at least 50° C. above the dew point of the outlet stream (i.e. the condensation temperature of the steam present in the outlet stream) at the actual pressure and composition thereof, the recycle stream being withdrawn after this cooling from the outlet stream and combined without further treatment with the inlet stream.

In effect this means that the improved process according to the invention for producing a methane rich gas in at least one adiabatically operated methanation reactor containing a bed of a methanation catalyst comprises, in combination, the steps of (a) supplying to the methanation reactor an inlet stream of a preheated methanation synthesis gas containing hydrogen and carbon monoxide (and often also carbon dioxide), the inlet stream being combined with a stream of a recycle gas and being passed through the catalyst bed, (b) operating the methanation reactor so as to provide an outlet stream having a temperature between 500° C. and 700° C., (c) cooling the outlet stream to a temperature between 250° C. and 350° C. and being at least 50° C. above the dew point of the outlet stream at the actual pressure and composition of that stream, (d) after the cooling withdrawing said recycle stream from the outlet stream and combining it without further treatment with the inlet stream and (e) passing the outlet stream on for further processing or for cooling and use as a desired ultimate product.

According to the invention it is very convenient to withdraw the recycle stream from the outlet stream by means of an ejector.

This may be carried out in various ways. Firstly, it is possible according to the invention to withdraw the recycle stream from the outlet stream by means of an ejector driven by the inlet stream. Secondly, it is possible according to the invention to withdraw the recycle stream from the outlet stream by means of an ejector driven by steam. In any of these situations, it is advantageous according to the invention to preheat the inlet stream to a temperature approximately the same as the temperature to which the outlet stream is cooled before the withdrawal of the recycle stream therefrom.

A methane synthesis gas suitable for methanation in a process according to this invention may have a dry gas composition within the following ranges, expressed in percent by volume: 10-50% carbon monoxide, 0-35% carbon dioxide, 40-80% hydrogen, and varying concentrations of methane depending upon the source of the synthesis gas.

Gases containing hydrogen and carbon monoxide are manufactured in large quantities by gasification of coal and by gasification of fuel oils. In such processes, the coal and fuel oil, respectively, is reacted at high temperatures with oxidizing gases containing oxygen, air, and/or steam. Depending upon its composition, the crude gas obtained from such processes must be subjected to various treatments before it is suitable for use as a methane synthesis gas. It will, normally, have to be purified for dust, tar products, solids, sulphur compounds, etc.

Furthermore, if the composition of the crude gas is far from being stoichiometric with respect to methane formation, it has been necessary in hitherto known processes to adjust the gas composition, for instance by converting part of its carbon monoxide with water to carbon dioxide and hydrogen according to reaction scheme (3) and by complete or partial removal of its carbon dioxide and steam, etc. However, it is an advantage of the process of this invention that it is rather flexible with respect to composition of the methane synthesis gas. This flexibility is in particular achieved because the process can be operated in such a way that the carbon monoxide conversion can take place in the methanation reactor simultaneously with the methanation reactions, and because a hot recycle is used. In this way, it is possible to compensate for deviations from stoichiometry by varying the concentration of steam present in the methane synthesis gas. Accordingly, a much wider range of synthesis gas composition can be used in the process of this invention than hitherto known processes. This means an improved economy of the process.

In cases where a product gas is desired which is equivalent to natural gas, i.e. rich in methane, the process of this invention should preferably be operated on a methane synthesis gas having a slight excess of carbon oxides. If appropriate operating conditions are selected, this excess of carbon oxides will be present in the final product gas as carbon dioxide which can be easily removed afterwards.

The methanation reactions are catalysed by various metals supported on suitable catalyst supports. Among such metals are cobalt, rhodium, palladium, platinum, ruthenium, and preferably nickel. A suitable methanation catalyst consists essentially of reduced nickel (i.e. metallic nickel) on a support material. Such a catalyst may be prepared by impregnating a decomposable nickel compound on the support or by precipitating a decomposable nickel compound together with the support. The nickel compound is then first converted to nickel oxide by calcination and thereafter reduced to metallic nickel prior to or during the methanation process.

A preferred methanation catalyst suitable for the methanation process in accordance with the present invention comprises nickel or nickel oxide together with an alumina-containing support. A particularly suitable catalyst consists essentially of nickel oxide together with an alumina/zirconia support material. Such a catalyst, in which nickel oxide may be present partly in chemical combination with alumina, may be prepared by the process described in our co-pending U.S. patent application Ser. No. 592,438. However, the process of this invention is not limited to the use of such a catalyst. Any nickel catalyst having a good activity at temperatures of about 300° C. and having good resistance up to temperatures of about 600° C. can be used.

The catalyst is arranged in a reactor having a fixed catalyst bed. The reactor may be a cylindrical vessel having a large diameter and the gas may pass upwards or preferably downwards through the catalyst bed in the axial direction. However, if pressure drop across the catalyst bed is a limiting factor, it may be preferable to arrange the catalyst in an annular bed through which the gas will pass inwards or outwards in the radial direction.

In many known processes it has been necessary to provide for cooling in the methanation reactor. Several means for such cooling have been suggested in the past. One suggestion was to subdivide the catalyst bed into several sections and provide cooling either by introducing cold synthesis gas between the sections or to withdraw the product from one section for cooling before passing it to a subsequent section. Another suggestion was to insert into the catalyst bed a number of tubes and to pass a fluid cooling medium through these tubes. It will be understood that a methanation reactor based on such principles is more complicated in construction as well as in operation than the methanation reactor used in the process of this invention. Therefore, the process of this invention has an overall improved economy compared to hitherto known processes.

It will be known and understood from the reaction schemes (1) and (2) that increasing pressure will tend to displace the equilibrium towards higher methane concentrations. Operation of the methanation process at high pressure is, therefore, an advantage. However, other considerations may also be applicable in the selection of the operating pressure. Normally, the process will be operated either at the pressure at which the methane synthesis gas is available or at the pressure at which the final product is required. If the product gas is intended for use as synthetic substitute for natural gas, it will preferably be produced at the pressure under which natural gas lines are operated, i.e. at about 50-90 atmospheres. If, however, the methane synthesis gas is available at a lower pressure, the methanation process may be operated at such lower pressure, for instance at about 20-40 atmospheres.

At the inlet to the methanation reactor the synthesis gas stream is combined with a recycle stream of hot product gas. The temperature of the combined streams should be as low as possible but high enough for the methanation reactions to initiate when the catalyst is contacted by the combined streams. A suitable inlet temperature will be between 250° and 350° C.

The ratio of recycle stream to synthesis gas inlet stream should be selected in accordance with the composition of the latter to give an outlet temperature between 500° and 700° C.

In selecting the recycle ratio, the risk of carbon formation will have to be considered. Although such a consideration will involve rather complicated calculations, sufficient thermodynamic data are available for a fairly good assessment of whether or not carbon formation will occur at the selected operating conditions. In this connection, it is an important advantage of the process of the present invention that it can be operated with added steam as well as without added steam in the methane synthesis gas, since addition of a certain amount of steam is an efficient means of avoiding carbon deposition in cases where there would otherwise be a risk of such carbon deposition.

In cases where a product gas having a high methane content is desired, two or more methanation reactors in series may be required. The product gas from the first reactor will be cooled to the inlet temperature used for the second reactor in which the gas is subjected to further methanation. Also in the second and any subsequent reactor product gas may be recycled; however, this is normally not necessary since the temperature increase will only be moderate in the second and possible subsequent reactors. Consequently, the process of the present invention is preferably used in connection with the first methanation reactor and further treatment of the product gas from the first reactor in subsequent reactors or other subsequent equipment does not form an essential part of the present invention.

An essential feature of the process of the present invention is that hot product gas is recycled to the methanation reactor by means of an ejector. Recycling of a gas stream which has been cooled to temperatures high enough to avoid condensation of steam is an advantage because of the better energy economy compared to processes where the recycle gas has to be cooled to temperatures below the condensation temperature. There may be several means for recycling such a hot gas stream. It has, however, been found that it is a considerable advantage to use an ejector for this purpose. The design of an ejector operating at high temperatures and pressures and at varying capacities is rather simple and such an ejector is relatively cheap. Consequently, in addition to an increase of the energy economy, the use of an ejector also contributes to an improvement of the overall economy of the methanation process.

Figure 2:
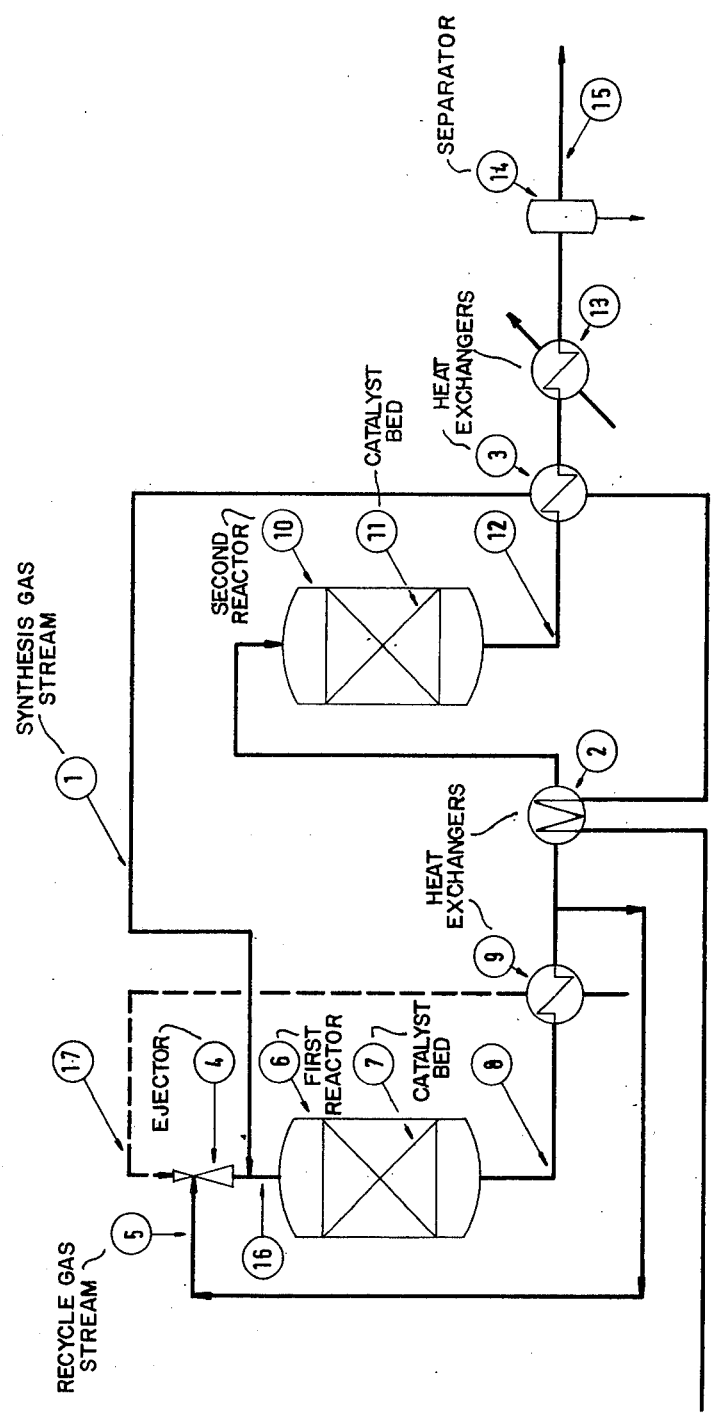

It is a particular advantage that in the process of this invention the ejector can either be driven by the methane synthesis gas or, when added steam is required, by high pressure steam. Either of these two embodiments presents considerable advantages and they will both be described with reference to the accompanying drawings, FIGS. 1 and 2, showing flow sheets of preferred embodiments of the invention. The flow sheet given in FIG. 1 relates to an embodiment in which the ejector is driven by the synthesis gas, while the flow sheet of FIG. 2 relates to an embodiment in which the ejector is driven by added high pressure steam generated in the methanation process itself or obtained from other sources.

Both figures show simplified process flow sheets in which a number of details have been omitted, such as gas blowers, compressors, details of coolers, heaters, and boilers, auxiliaries for controlling temperatures, pressure, flow, etc. Only the principal features essentially related to the invention have been included in these flow sheets, since once such features have been disclosed, it will be obvious to those skilled in the art how to work out detailed flow sheets and designs for processes incorporating such features. Particularly, it is known in the art or obvious how to integrate heating and cooling systems in the form of heat exchangers, boilers, etc. to give an optimum energy economy of the process.

In FIG. 1 a methane synthesis gas stream 1 available at elevated pressure is heated to the desired temperature in heat exchangers 2 and 3 by the product gas streams from a first methanation reactor 6 and a second methanation reactor 10, respectively. In ejector 4 the synthesis gas stream is combined with a recycle gas stream 5 drawn from the outlet stream from the first methanation reactor 6. In order to create the necessary driving force for the ejector to withdraw the recycle gas stream 5, the synthesis gas stream 1 must be available at a pressure slightly higher than the pressure required at the inlet to the methanation reactor.

The combined streams of synthesis gas 1 and recycle gas 5 enter the first methanation reactor 6 through line 16 and pass through the catalyst bed 7 situated in reactor 6. The outlet stream 8 from the first methanation reactor 6, now heated to a higher temperature by the exothermic reactions, is cooled in heat exchanger 9 which is operated as a high pressure steam generator. After withdrawal of the recycle gas stream 5, the product gas stream from the first reactor may be further cooled in heat exchanger 2 and passed to the second methanation reactor 10 and through catalyst bed 11 contained therein.

The outlet stream or product gas stream from the second methanation reactor 10 is cooled in heat exchangers 3 and 13. Steam is removed in separator 14 and the final product gas stream 15 is obtained.

In FIG. 2 most of the flow sheet is unchanged from FIG. 1 and same numerals are used to designate identical gas streams and pieces of equipment. Therefore, only the differences resulting from driving the ejector 4 by high pressure steam will be described here. The added steam for driving the ejector is high pressure steam generated in heat exchanger 9 from where it is passed to the ejector through line 17. In this case the methane synthesis gas stream 1 is passed directly to the first methanation reactor through line 16 and no excess of pressure is required as in the case illustrated in FIG. 1.

EXAMPLES

Eight examples of operating data are given in Table I for further illustration of the operation of the process of the present invention on various methane synthesis gases and with the ejector driven by high pressure steam (Examples 4, 5, 7, and 8) or with methane synthesis gas (Examples 1, 2, 3, and 6).

The final product gas obtained in some of the Examples (particularly Examples 2, 3, and 4) still contains some hydrogen and carbon dioxide. Therefore, if a methane concentration above 90 vol. % is desired, the outlet stream 12 from the second methanation reactor could, after cooling to 250°–300° C., be subjected to further methanation in a third methanation reactor. However, since this does not form an essential part of this invention, it has not been shown on the flow sheets. In the remaining examples (Examples 1, 5, 6, 7, and 8) the methane concentration is either above 90 vol % or it can be increased to more than 90 vol % by a simple removal of carbon dioxide. This is particularly the case in Examples 5 and 8 where removal of the carbon dioxide would give gases containing 97.5% and 94.5% methane, respectively.

reactor to a temperature of between 500° C. and 700° C.,

Table I

| Example No. | 1 | 2 | 3 | 4 | 5 | 6 | 7 | 8 |
|---|---|---|---|---|---|---|---|---|
| Driving Medium for Ejector | Gas | Gas | Gas | Steam | Steam | Gas | Steam | Steam |
| Synthesis Gas Stream 1: | | | | | | | | |
| Rate, Nm$^3$/h | 100,000 | 100,000 | 100,000 | 100,000 | 100,000 | 100,000 | 100,000 | 100,000 |
| Pressure, atm.abs. | 74 | 36 | 30 | 30 | 30 | 30 | 30 | 30 |
| Temperature, °C | 300 | 300 | 300 | 300 | 300 | 300 | 300 | 300 |
| Composition: vol% H$_2$ | 48.7 | 75.1 | 66.8 | 66.8 | 49.8 | 48.7 | 48.7 | 40.0 |
| vol% CO | 16.1 | 24.1 | 19.4 | 19.4 | 49.8 | 16.1 | 16.1 | 20.0 |
| vol% CO$_2$ | 0.1 | 0.1 | 2.7 | 2.7 | 0.1 | 0.1 | 0.1 | 28.0 |
| vol% CH$_4$ | 35.1 | 0.0 | 11.1 | 11.1 | 0.3 | 35.1 | 35.1 | 11.0 |
| vol% H$_2$O | 0.0 | 0.0 | 0.0 | 0.0 | 0.0 | 0.0 | 0.0 | 0.0 |
| vol% inerts | 0.0 | 0.7 | 0.0 | 0.0 | 0.0 | 0.0 | 0.0 | 1.0 |
| Combined Gas Stream 16 entering Reactor 6: | | | | | | | | |
| Rate, Nm$^3$/h | 250,000 | 400,000 | 300,000 | 313,686 | 636,800 | 300,000 | 210,000 | 335,430 |
| Pressure, atm.abs. | 71 | 29 | 26 | 30 | 30 | 26 | 30 | 30 |
| Temperature, °C | 300 | 300 | 300 | 300 | 300 | 300 | 300 | 300 |
| Composition: vol% H$_2$ | 25.9 | 34.1 | 36.8 | 34.5 | 12.5 | 23.6 | 32.0 | 15.4 |
| vol% CO | 6.7 | 6.8 | 7.6 | 6.9 | 8.5 | 5.6 | 8.2 | 6.8 |
| vol% CO$_2$ | 1.4 | 3.2 | 4.2 | 4.0 | 22.4 | 1.6 | 1.8 | 29.5 |
| vol% CH$_4$ | 55.4 | 29.2 | 33.5 | 26.5 | 23.0 | 57.3 | 42.8 | 18.7 |
| vol% H$_2$O | 10.6 | 25.8 | 17.9 | 28.1 | 33.6 | 11.9 | 15.2 | 28.5 |
| vol% inerts | 0.0 | 0.9 | 0.0 | 0.0 | 0.0 | 0.0 | 0.0 | 1.1 |
| Outlet Stream 8 from Reactor 6: | | | | | | | | |
| Rate, Nm$^3$/h | 221,678 | 356,470 | 264,390 | 279,200 | 591,500 | 272,000 | 186,060 | 308,790 |
| Temperature, °C | 576 | 601 | 617 | 606 | 518 | 530 | 602 | 520 |
| Composition: vol% H$_2$ | 10.8 | 20.5 | 21.7 | 20.7 | 6.1 | 11.0 | 18.4 | 5.5 |
| vol% CO | 0.5 | 1.0 | 1.7 | 1.1 | 1.1 | 0.4 | 1.2 | 1.3 |
| vol% CO$_2$ | 2.3 | 4.1 | 4.9 | 5.0 | 28.3 | 2.3 | 3.7 | 33.8 |
| vol% CH$_4$ | 68.7 | 38.9 | 44.8 | 35.9 | 28.7 | 68.6 | 54.8 | 24.6 |
| vol% H$_2$O | 17.7 | 34.5 | 26.9 | 37.3 | 35.8 | 17.7 | 21.9 | 33.6 |
| vol% inerts | 0.0 | 1.0 | 0.0 | 0.0 | 0.0 | 0.0 | 0.0 | 1.2 |
| Recycle Gas Stream 5: | | | | | | | | |
| Rate, Nm$^3$/h | 150,000 | 300,000 | 200,000 | 200,000 | 503,500 | 200,000 | 100,000 | 210,130 |
| Pressure, atm.abs. | 70.5 | 28.5 | 25.5 | 29.5 | 29.5 | 25.5 | 29.5 | 29.5 |
| Temperature, °C | 300 | 300 | 300 | 300 | 300 | 300 | 300 | 300 |
| Product Gas Stream 8 entering Reactor 10: | | | | | | | | |
| Rate, Nm$^3$/h | 71,678 | 56,470 | 64,390 | 79,201 | 88,000 | 72,000 | 86,060 | 98,650 |
| Temperature, °C | 250 | 300 | 250 | 250 | 250 | 300 | 300 | 250 |
| Product Gas Stream 12 leaving Reactor 10: | | | | | | | | |
| Rate, Nm$^3$/h | 68,271 | 52,600 | 58,922 | 72,914 | 85,270 | 69,090 | 80,290 | 95,600 |
| Temperature, °C | 347 | 454 | 444 | 432 | 326 | 380 | 444 | 326 |
| Composition: vol% H$_2$ | 1.8 | 8.3 | 7.0 | 6.4 | 0.7 | 3.5 | 6.6 | 0.6 |
| vol% CO | 0.0 | 0.1 | 0.1 | 0.0 | 0.0 | 0.0 | 0.1 | 0.0 |
| vol% CO$_2$ | 0.4 | 1.7 | 2.5 | 2.2 | 28.8 | 0.7 | 1.6 | 34.6 |
| vol% CH$_4$ | 74.7 | 45.4 | 53.5 | 43.4 | 31.3 | 73.5 | 62.3 | 27.0 |
| vol% H$_2$O | 23.1 | 43.4 | 36.9 | 48.0 | 39.2 | 22.3 | 29.4 | 36.5 |
| vol% inerts | 0.0 | 1.1 | 0.0 | 0.0 | 0.0 | 0.0 | 0.0 | 1.3 |
| Final Product Gas Stream 15: | | | | | | | | |
| Rate, Nm$^3$/h | 52,555 | 26,680 | 37,257 | 37,951 | 51,900 | 53,700 | 56,600 | 60,500 |
| Pressure, atm.abs. | 69 | 27.5 | 24.5 | 28.5 | 28.5 | 24.5 | 28.5 | 28.4 |
| Temperature, °C | 30 | 30 | 30 | 30 | 30 | 30 | 30 | 30 |
| Composition: vol% H$_2$ | 2.3 | 14.7 | 11.0 | 12.2 | 1.2 | 4.5 | 9.4 | 0.3 |
| vol% CO | 0.0 | 0.2 | 0.1 | 0.1 | 0.0 | 0.0 | 0.1 | 0.0 |
| vol% CO$_2$ | 0.5 | 3.0 | 4.0 | 4.3 | 47.2 | 0.9 | 2.3 | 54.6 |
| vol% CH$_4$ | 97.1 | 80.2 | 84.7 | 83.2 | 51.4 | 94.4 | 88.0 | 42.9 |
| vol% H$_2$O | 0.1 | 0.1 | 0.2 | 0.2 | 0.2 | 0.2 | 0.2 | 0.2 |
| vol% inerts | 0.0 | 2.0 | 0.0 | 0.0 | 0.0 | 0.0 | 0.0 | 2.0 |

We claim:

1. In a process for producing a methane rich gas in at least one adiabatically operated methanation reactor in which process an inlet stream of a preheated methane synthesis gas containing 40–80% hydrogen, 0–35% carbon dioxide and 10–50% carbon monoxide is combined with a recycle stream of product gas from the methanation reactor to form a combined stream which thereafter is passed through a bed of a methanation catalyst contained in the methanation reactor, the outlet stream from the methanation reactor being divided into the recycle stream and a stream of product gas to be passed on, the improvement which comprises the steps of:
   (a) in forming the combined stream, the ratio of the recycle stream to the inlet stream being selected within a range of from 1:1 to 5:1 to provide in the combined stream such contents of hydrogen and carbon oxides which upon methanation to equilibrium produce sufficient heat to raise the temperature of the outlet stream leaving the methanation reactor to a temperature of between 500° C. and 700° C.,
   (b) cooling the outlet stream from the temperature of between 500° C. and 700° C. to a temperature of between 250° C. and 350° C. and being at least 50° C. above the dew point of the outlet stream at its actual pressure and composition, and
   (c) after the cooling in step (b) and substantially at the temperature obtained therein, withdrawing the recycle stream from the outlet stream by means of an ejector and without further treatment combining it with the inlet stream.

2. The process of claim 1 wherein the ejector is driven by the inlet stream, and wherein the inlet stream is preheated to a temperature approximately the same as that to which the outlet stream is cooled before the withdrawal of the recycle stream therefrom.

3. The process of claim 1 wherein the ejector is driven by steam which thereby combines with the inlet stream and the recycle stream to be made part of the combined stream, and wherein the inlet stream is preheated to a temperature approximately the same as that to which the outlet stream is cooled before the withdrawal of the recycle stream therefrom.

* * * * *